United States Patent
Ramdas et al.

(10) Patent No.: US 9,327,105 B2
(45) Date of Patent: May 3, 2016

(54) ACTIVE TRANSDERMAL DRUG DELIVERY SYSTEM AND THE METHOD THEREOF

(75) Inventors: Radhakrishnan Ramdas, Seccunderabad (IN); Kartik Karri, Seccunderabad (IN); Chidella Venkata Krishna Mohan Sharma, Seccunderabad (IN)

(73) Assignee: ITRACE BIOMEDICAL INC., Milpitas, CA (US)

( * ) Notice: Subject to any disclaimer, the term of this patent is extended or adjusted under 35 U.S.C. 154(b) by 45 days.

(21) Appl. No.: 13/064,334

(22) Filed: Mar. 21, 2011

(65) Prior Publication Data
US 2011/0264028 A1   Oct. 27, 2011

(30) Foreign Application Priority Data

Mar. 26, 2010   (IN) .............................. 819/CHE/2010

(51) Int. Cl.
| | | |
|---|---|---|
| *A61M 37/00* | (2006.01) | |
| *A61M 5/00* | (2006.01) | |
| *A61M 35/00* | (2006.01) | |
| *A61M 5/142* | (2006.01) | |
| *A61F 13/40* | (2006.01) | |

(Continued)

(52) U.S. Cl.
CPC ....... *A61M 37/0092* (2013.01); *A61M 5/14248* (2013.01); *A61M 35/006* (2013.01); *A61M 37/00* (2013.01); *A61K 9/0009* (2013.01); *A61M 2037/0007* (2013.01); *A61N 1/0428* (2013.01); *A61N 1/0492* (2013.01); *A61N 1/325* (2013.01)

(58) Field of Classification Search
CPC ................. A61M 37/0092; A61M 2037/0007; A61M 37/0015; A61M 2037/0046; A61M 2037/0023; A61M 5/14248; A61N 1/30; A61N 1/325; A61N 1/0428; A61N 1/327; A61N 7/00; A61N 1/0412; A61N 1/0476; A61N 1/0492; A61N 2007/0034; A61N 2007/0078
USPC .......................... 604/20, 49; 607/2; 424/449
See application file for complete search history.

(56) References Cited

U.S. PATENT DOCUMENTS

| | | | |
|---|---|---|---|
| 4,286,592 A | * | 9/1981 | Chandrasekaran A61F 13/00063 424/448 |
| 4,404,460 A | | 9/1983 | Kerr |

(Continued)

OTHER PUBLICATIONS

Park et al., "The effect of heat on skin permeability", International Journal of Pharmaceutics, 2008, vol. 359, p. 94-103.

(Continued)

*Primary Examiner* — Kevin C Sirmons
*Assistant Examiner* — William Carpenter
(74) *Attorney, Agent, or Firm* — Kilpatrick Townsend & Stockton LLP

(57) ABSTRACT

The present invention relates to an active transdermal drug delivery system performing transdermal drug delivery comprising of a patch capable of being attachable to the skin of the subject; at least one electrical energy power input; a plurality of converters/energy transducers configured for converting the electrical energy to different forms of energy; and a controller including a programmable microprocessor configured for providing the intensity, sequence, nature, and timing information for the different energies supplied and thereby providing activating signals to the said converters for the transdermal drug delivery by the said patch, and a method for performing transdermal drug delivery using said electronic patch.

28 Claims, 5 Drawing Sheets

(51) Int. Cl.
*A61K 9/00* (2006.01)
*A61N 1/04* (2006.01)
*A61N 1/32* (2006.01)

(56) References Cited

U.S. PATENT DOCUMENTS

| | | | |
|---|---|---|---|
| 4,736,088 A | 4/1988 | Bart | |
| 4,823,775 A | 4/1989 | Rindt | |
| 5,036,861 A | 8/1991 | Sembrowich et al. | |
| 5,076,273 A | 12/1991 | Schoendorfer et al. | |
| 5,139,023 A | 8/1992 | Stanley et al. | |
| 5,140,985 A | 8/1992 | Schroeder et al. | |
| 5,279,543 A | 1/1994 | Glikfeld et al. | |
| 5,421,816 A | 6/1995 | Lipkovker | |
| 5,658,247 A * | 8/1997 | Henley | A61N 1/30 604/20 |
| 5,667,487 A * | 9/1997 | Henley | 604/20 |
| 5,697,896 A | 12/1997 | McNicholas et al. | |
| 5,722,397 A | 3/1998 | Eppstein | |
| 5,833,647 A * | 11/1998 | Edwards | 604/22 |
| 5,860,957 A * | 1/1999 | Jacobsen et al. | 604/156 |
| 5,902,603 A * | 5/1999 | Chen et al. | 424/449 |
| 5,935,598 A * | 8/1999 | Sage et al. | 424/449 |
| 5,947,921 A * | 9/1999 | Johnson | A61B 5/14514 601/2 |
| 5,948,012 A | 9/1999 | Mahaffey et al. | |
| 6,180,416 B1 | 1/2001 | Kurnik et al. | |
| 6,251,083 B1 | 6/2001 | Yum et al. | |
| 6,261,595 B1 | 7/2001 | Stanley et al. | |
| 6,334,856 B1 * | 1/2002 | Allen et al. | 604/191 |
| 6,527,716 B1 * | 3/2003 | Eppstein | 600/309 |
| 6,623,457 B1 | 9/2003 | Rosenberg | |
| 6,649,886 B1 | 11/2003 | Kleshchik | |
| 6,662,044 B2 | 12/2003 | Crawford et al. | |
| 6,692,456 B1 | 2/2004 | Eppstein et al. | |
| 7,650,177 B2 | 1/2010 | Hoarau et al. | |
| 2002/0055702 A1 * | 5/2002 | Atala | A61M 37/0092 604/20 |
| 2002/0114827 A1 * | 8/2002 | Zhang et al. | 424/449 |
| 2002/0156415 A1 * | 10/2002 | Redding, Jr. | 604/22 |
| 2003/0023151 A1 | 1/2003 | Khalil et al. | |
| 2003/0225360 A1 * | 12/2003 | Eppstein et al. | 604/19 |
| 2005/0283110 A1 * | 12/2005 | Atala et al. | 604/20 |
| 2007/0083186 A1 * | 4/2007 | Carter | A61N 1/044 604/501 |

OTHER PUBLICATIONS

Non-Final Office Action for U.S. Appl. No. 13/428,670, mailed on Oct. 29, 2013, 16 pages.
Final Office Action for U.S. Appl. No. 13/428,670, mailed Mar. 21, 2014, 15 pages.
Non-Final Office Action for U.S. Appl. No. 13/428,670, mailed on Sep. 29, 2014, 16 pages.

* cited by examiner

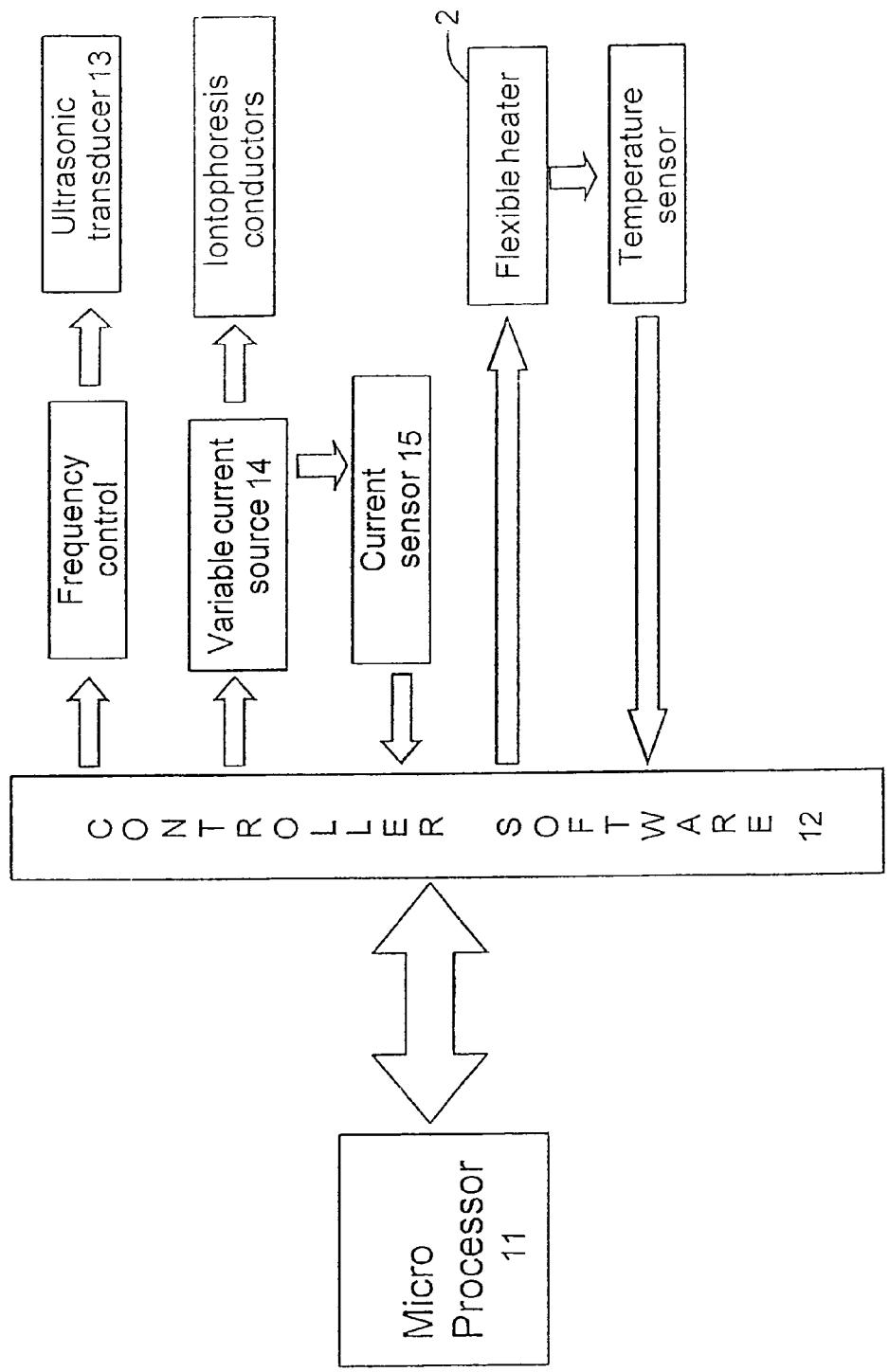
Fig. 3 Block Diagram of Transdermal Drug Delivery System

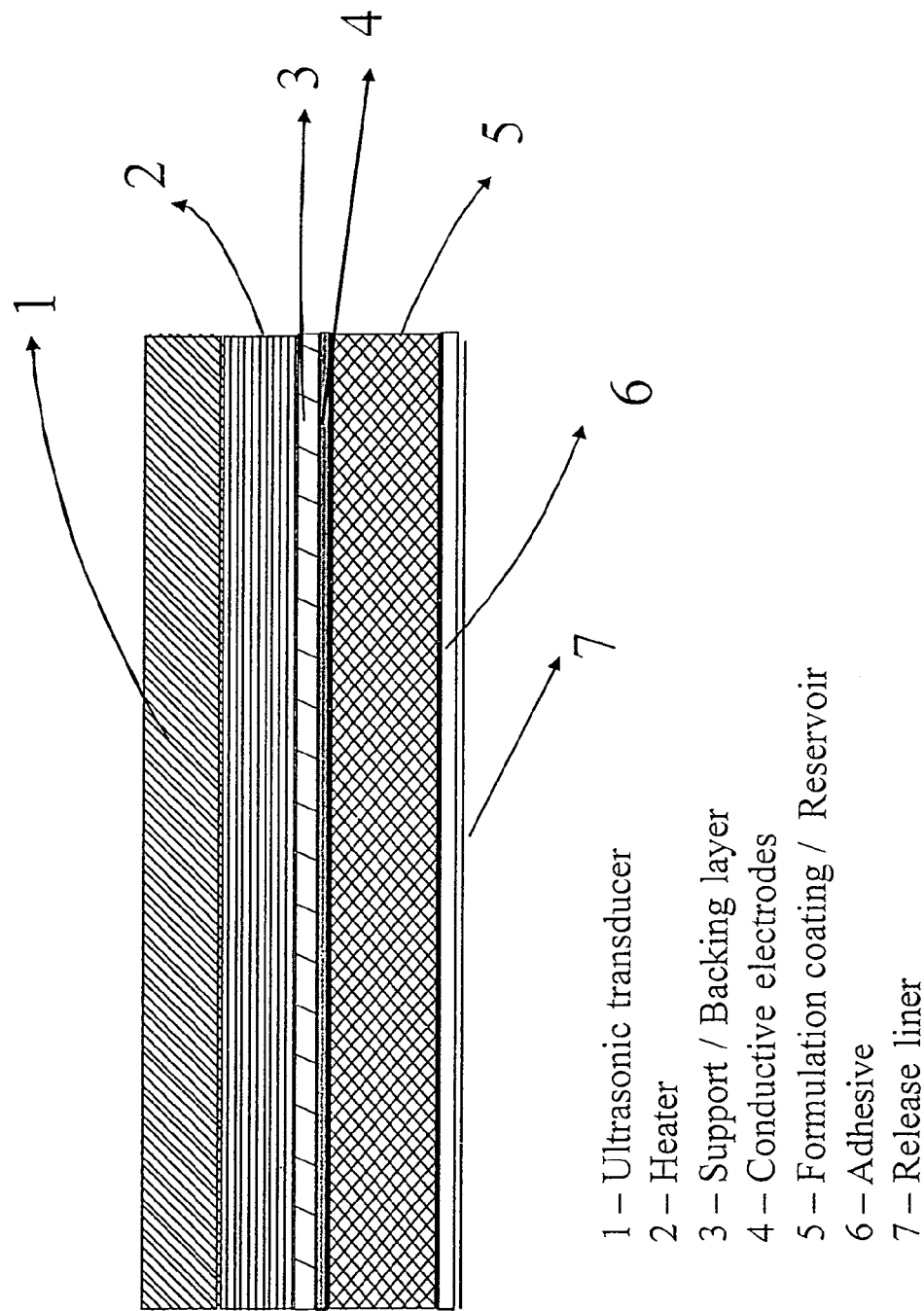
Fig. 4(a) Schematic Cross Section of the Transdermal Patch
1 – Ultrasonic transducer
2 – Heater
3 – Support / Backing layer
4 – Conductive electrodes
5 – Formulation coating / Reservoir
6 – Adhesive
7 – Release liner

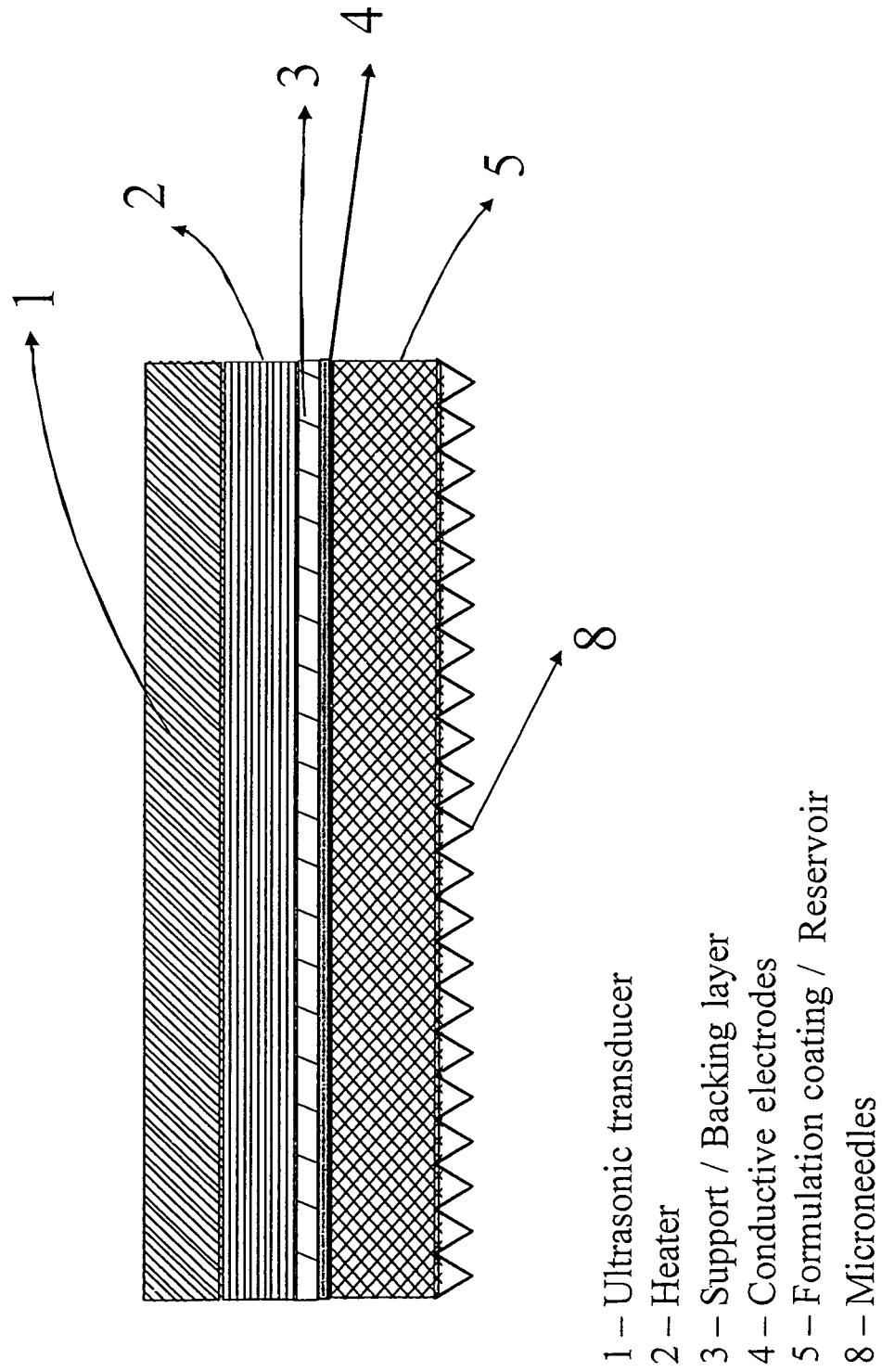
Fig. 4(b) Another Schematic Cross Section of the Transdermal Patch
1 – Ultrasonic transducer
2 – Heater
3 – Support / Backing layer
4 – Conductive electrodes
5 – Formulation coating / Reservoir
8 – Microneedles

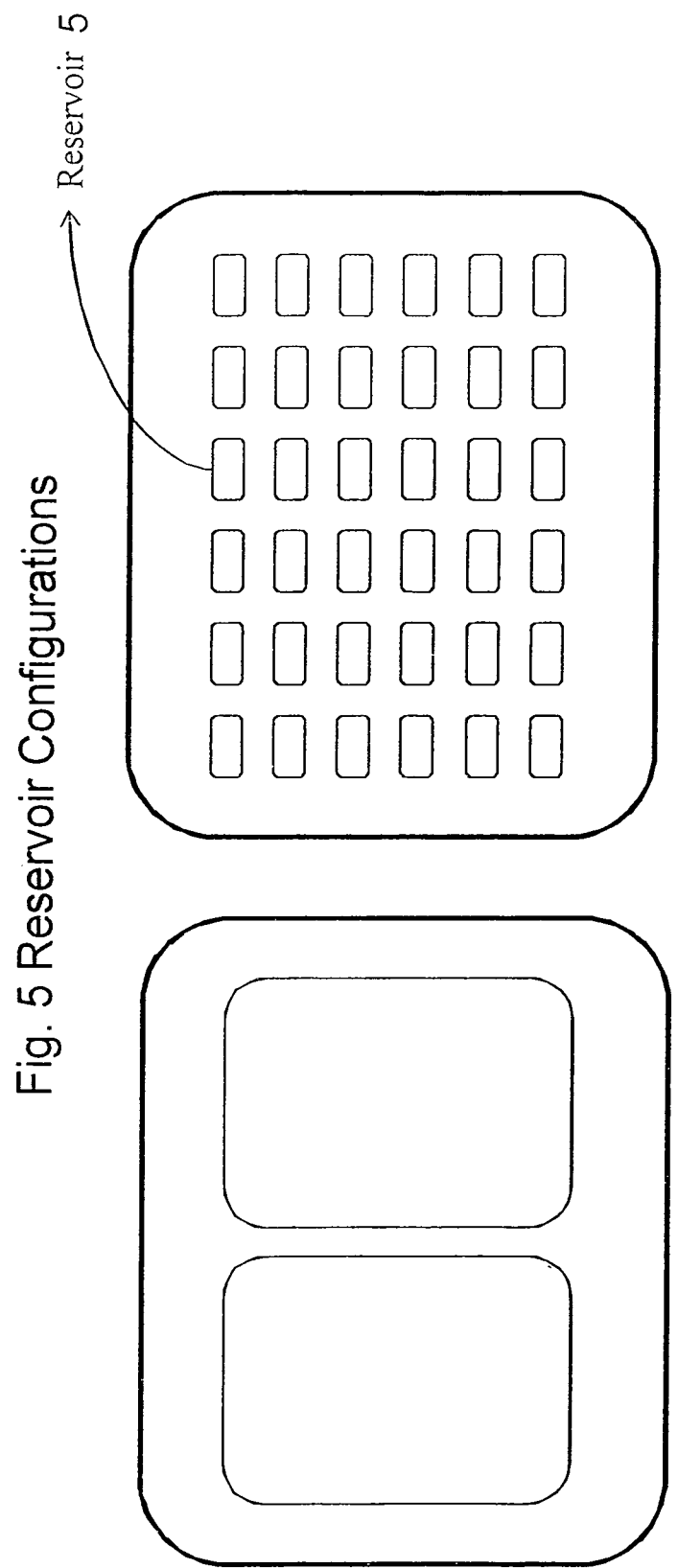
Fig. 5 Reservoir Configurations

ACTIVE TRANSDERMAL DRUG DELIVERY SYSTEM AND THE METHOD THEREOF

FIELD OF INVENTION

Foreign Priority

The present application claims priority to Indian Patent Application 819/CHE/2010. The entire disclosure contents of this document is herewith incorporated by reference into the present application.

BACKGROUND ART

Transdermal drug delivery provides several important advantages over traditional oral and intravenous delivery routes as it bypasses the liver in terms of first pass elimination, avoids the inconvenience of intravenous therapy, provides less chance of dosage errors, permits steady absorption of drugs over longer time periods and enables both local and systemic treatment effects. A variety of transdermal drug delivery systems are currently available in the market and/or in developmental stage that use a single source of energy to enhance skin permeability and have limitations in their applicability. Transdermal drug delivery systems depend on a variety of well established technologies and transport mechanisms to facilitate the migration of drugs across the skin membrane. Despite the advances made in transdermal delivery systems, skin permeability (especially for larger molecules such as insulin and vaccines) and the controlled delivery of smaller molecules with desirable/programmable release profiles (e.g., pulsatile delivery) on a single platform is not available.

For example, T. Stanley et. al (U.S. Pat. No. 6,261,595) discusses a transdermal drug delivery system comprising a heating element, where the application of heat facilitates the active transport of the drug across the skin membrane. Recently, J. Park et. al. (International Journal of Pharmaceutics, 2008, 359, 94-103) reported that exposing the skin to higher temperatures (>100° C.) for shorter times (less than a second) leads to higher skin permeability without damaging the skin. Heat induced delivery enhances kinetic energy of drug molecules and the proteins, lipids, and carbohydrates in the cell membrane leading to higher skin permeability, body fluid circulation, blood vessel wall permeability, and drug solubility. Heating prior to or during topical application of a drug dilates the penetration pathways in the skin, while heating the skin after the topical application of a drug increases the drug absorption into the vascular network, enhancing the systemic delivery but decreasing the local delivery as the drug molecules are carried away from the local delivery site. Further, it is also possible that application of focused thermal energy in short bursts (>100° C.) porate the skin (thermal ablation of stratum corneum) and enable drug permeation.

It has been established that application of ultrasound radiation/pressure on the skin also increases transdermal penetration rate. The mechanism of action was attributed to micro channel formation via cavitation and/or radiation pressure onto the drug (U.S. Pat. No. 5,421,816). The idea of using electrically assisted transmembrane drug delivery (e.g., iontophoresis) was described by L. A. McNichols in the U.S. Pat. No. 5,697,896, where the electromotive force (repulsive charges) act upon drug molecules charged or uncharged or mixture thereof. Electroporation is another form of electrically assisted transportation of molecules, where a quick voltage shock disrupts areas of the membrane temporarily and permeates drug molecules. For example, N. Crawford et. al. (U.S. Pat. No. 6,662,044) use a combination of iontophoresis and electroporation.

Recently, there have also been studies on microneedle based transdermal drug delivery patches, and the rationale behind this technology is that needles ranging from 100 to 1500 microns (opening diameter ranges from 10 to 300 microns) in lengths offer less painful and efficient route for transdermal drug delivery. Arrays of microneedles inserted across the stratum corneum have been shown to painlessly disrupt this barrier and increase the permeability of skin by several fold magnitude (i.e., without applying any active energy form). Microneedles arrays based substrates are typically based on metal (e.g., steel), polymer or biodegradable (e.g., polylactic acid, polyglycolic acid and their copolymers) or metal oxides (e.g., silicon dioxide). However, unfortunately, the efficiency of the micro needle technology is dependent on shape, width and size of the needle and the drug diffusion into the skin is passive and is not well controlled. For example Zeil B Rosenberg (U.S. Pat. No. 6,623,457) describes method of transdermal delivery of pharmaceutical agent by employing microneedles.

As outlined above varieties of energy forms (and an array of microneedles) have been used to transport the drug across the skin membrane, which may involve multitude of drug transport mechanisms. However, unfortunately, each energy form has its own preferred transport mechanism and may have limitations with regard to the number and type of drugs they could delivery across the skin membrane. Besides the drug permeation rates dramatically vary depending upon drug/formulation and the nature of energy form applied. In this regard, we propose the use of a single controller that provides a combination of energy sources/pulses to act upon a transdermal drug delivery patch (including microneedles based) with varying intensity, sequence, and timing to enable the transport of drugs using synergistic/cooperative transport mechanisms. As a consequence, application of multiple energy forms in a predetermined sequence/time intervals and intensities provides an excellent opportunity to permeate several small and large molecular drugs (including insulin and vaccines) and provides precise control over pharmacokinetics and drug transport mechanisms leading to the emergence of a single platform that treats multiple therapeutic indications that have been disclosed herein.

In this venture, we take advantage of recent advances in printed electronics/microneedle arrays to deliver drugs transdermally using a combination of transport mechanisms and energy sources, i.e., heat, sound and electromotive force, where a microprocessor controls the thermal/ultrasonic energy and electrical current applied to the skin in a programmable fashion (concurrently or alternately) to deliver drugs (e.g., insulin) with tunable pharmacokinetics for local and systemic drug delivery applications.

Further, the disclosure is intended to generate a new disposable active transdermal patch for delivering a variety of drugs (including insulin and vaccines) with controlled pharmacokinetics. Current transdermal drug delivery patches rely on unregulated energy sources and have limitations in delivering drugs of choice (i.e., small molecules to vaccines) e with controllable pharmacokinetics.

SUMMARY OF THE INVENTION

Using the present invention, we herein disclose the development a novel active transdermal patch (including microneedle based arrays) that delivers drugs using a combination of energy sources such as heat, sound and electricity (i.e., iontophoresis or electroporation) synergistically to accomplish the enhanced skin permeability of small or large molecules with tunable pharmacokinetics on a single platform for both local and systemic drug delivery applications.

Therefore the primary object of the present invention is to provide an active transdermal skin patch driven by a controller (which includes a programmable processor) that provides the application of a combination of energy sources with varying intensity, sequence, and timing to enable the transport of drugs using synergistic/cooperative permeation mechanisms. Thereby, improve the skin permeability of smaller and larger molecules and accomplish controllable drug release profiles through transdermal drug delivery system. In addition, the development of an active transdermal patch that receives signals from controller and propels the drug into the skin.

The skin permeability response to the application of combination of energy source pulsing sequences/intensities in tandem for a given drug/formulation properties are optimized experimentally to develop a best possible pharmacokinetic profile for a given therapeutic indication. Therefore, the drug delivery could be highly customized for a given drug/cosmetic and for a particular patient/disease and further may also enable the patient/physician to titrate the drug to personalize the drug dosage and kinetic profile for individual patients needs.

It is an object of the present invention to provide an electronically controlled versatile drug delivery system It is also an object of the present invention to provide a programmable electronic drug delivery system controller that provides automatic drug administration without the need of any assistance.

It is another object to provide a drug delivery method and system that can store and administer a plurality of doses of a single or multiple drugs at periodic programmed or on demand intervals.

It is another object of the present invention to provide a drug delivery system that can store and administer a plurality of different drugs.

It is another object of the present invention to provide sensors for feedback on patient status and thereby enabling the controller to commence the drug delivery if sensors indicate a need and can administer drugs using a plurality of different delivery profiles.

As per an exemplary embodiment of the present invention there is provided an active transdermal patch with or without microneedle based arrays and/or perforations that transdermally delivers drug by accepting a combination of energy pulses along with a configured controller comprising power source (battery/capacitor) and which includes a microprocessor that programs the intensity, sequence and timing of the different energies supplied to the active transdermal patch.

The improved active transdermal patch is configured for the treatment of large areas of skin where the patch enhances the penetration of substances like antibiotic, antifungal or growth factors when driven into a tissue to promote healing and minimize infection.

another object of this invention is to describe the construction of an active transdermal patch, where a power source is provided in the form of a battery or a capacitor for driving a circuitry comprising a plurality of convertors for converting electrical energy into the desired different forms of energy for greatly enhanced skin penetration of medications, hormones peptides and other therapeutic substances.

It is an additional object of the present invention to provide an improved versatile active transdermal patch medicament applicator that can be configured for multiple use in transdermal drug delivery and further used to treat a large dermal area.

It is yet another object of the present invention to minimize the skin patch size (surface area) for certain applications by taking advantage of rapid/active drug delivery profiles obtained from the proposed transdermal drug delivery system.

To achieve the foregoing objectives and in accordance with the present invention as embodied and broadly described herein, the present invention discloses an electronic patch performing transdermal drug delivery comprising of at least one electrical energy power input; a controller including a microprocessor configured for providing the intensity, sequence, nature, and timing information for the different energies supplied to the said patch; a plurality of converters configured for converting the electrical energy to different forms of energy on getting activated by the said controller.

Herein it is also disclosed a method for performing transdermal drug delivery using an electronic patch comprising the steps of inputting electrical energy from a power source; controlling the electrical energy power input using a controller; converting the electrical energy to different forms of energy using converters; and providing the intensity, sequence, nature, and timing signals for the different energies supplied to the said patch which are provided by a configured microprocessor.

A further embodiment of the present invention provides a support material for transdermal patch which is a thin flexible sheet made of polymer, or rubber, or resin, or textile, or a thin metal acceptable for medical applications. At least a part of the support material may have some kind of adhesive to stick it to the skin and may be perforated. Optionally, the support material provides backing and protects the patch from the outer environment.

A further embodiment of the present invention provides a support material (metal, metal oxide or polymer) that has an array of microneedles. The tips can be anything from tapered, conical, chisel or bevel. The needles can vary in lengths from 150 µm to even 1500 µm and the tip diameter 10-300 µm. Ideally, the microneedles will only penetrate deep enough to pass the first ~15 µm of skin, the barrier known as the stratum corneum.

A further embodiment of the present invention is to provide a patch which is in a shape of a tattoo for attracting the customers.

A further embodiment of the present invention is to include a timer circuitry for regulating dosage requirements to ensure the safety of patients.

A further embodiment of the present invention provides a transdermal patch with an outer protective coating/sheet or liner or tab which is removed prior to use.

A further embodiment of the present invention is to provide a feedback control mechanism which provides further control over the medicament delivery.

A yet further embodiment of the present invention provides sensors in the active transdermal patch and enable data collection to the feedback control mechanism and the controller.

Additional objects and the advantages of the invention will be set forth in the description which follows and in part will be obvious from the description or may be learned by the practice of the invention. The objects and the advantages of the invention may be realized and obtained by means of the instruments and combinations particularly pointed out in the appended claims.

BRIEF DESCRIPTION OF THE DRAWINGS

FIG. 3 illustrates a block diagram of transdermal drug delivery system of the present invention.

FIG. 4(a) shows the schematic representation of a cross section of the transdermal patch of the present invention.

FIG. 4(b) shows another schematic representation of a cross section of the transdermal patch of the present invention.

FIG. 5 illustrates the schematic representation of the reservoir used in the transdermal patch of the present invention.

DETAILED DESCRIPTION

Figure 1:
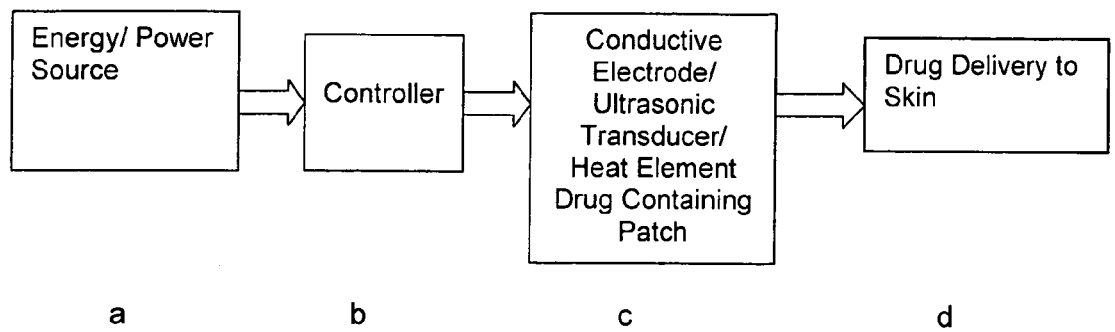
FIG. 1 illustrates the schematic representation of active transdermal drug delivery system in accordance with the present invention.

Transdermal drug delivery provides several important advantages over traditional oral and intravenous delivery routes as it bypasses the liver in terms of first pass elimination, avoids the inconvenience of intravenous therapy, permits steady absorption of drugs over longer time periods and enables both local and systemic treatment effects. Transdermally delivered drugs have been used to treat a variety of diseases such as hormonal imbalance (testosterone, estrogen), vasodilation (nitroglycerin), smoking cessation (nicotine), pain relief (fentanyl, a potent opioid), while on cosmoceutical front the symptoms being treated include, anti-aging, anti wrinkle, puffiness and dark circles, and anticellulite. Transdermal drug delivery mechanisms include poration (i.e., high-frequency pulses of sonic/electric/thermal energy or microneedles that temporarily disrupt the stratum corneum), iontophoresis, magnetism and heat. Transdermal delivery of several new drugs that are currently underway by various organizations use one of the above mechanisms/energy sources. However, delivering/controlling pharmacokinetics of smaller and/or larger molecules using any single mechanism or energy source has limited applications in terms of the choice of molecules and/or pharmacokinetics one could deliver/accomplish.

To overcome the fundamental limitations in transporting drug across the membrane, as discussed in detail in the above sections, we propose the use of an active transdermal patch, where multiple energy forms synchronously and synergistically trigger combinations of drug transport mechanisms to attain desired drug delivery profiles is disclosed herein in detail for understanding the invention clearly and sufficiently. Heat induced delivery enhances kinetic energy of drug molecules and the proteins, lipids, and carbohydrates in the cell membrane to promote the skin permeability, body fluid circulation, blood vessel wall permeability, and drug solubility. Heating prior to or during topical application of a drug dilates the penetration pathways in the skin, while heating the skin after the topical application of a drug increases the drug absorption into the vascular network, enhancing the systemic delivery but decreasing the local delivery as the drug molecules are carried away from the local delivery site. It is also possible to use focused thermal energy in short bursts to porate the skin (thermal ablation of stratum corneum). While electricity (e.g., iontophoresis) propels charged drug compounds (and neutral in some cases) transdermally in the presence of an electric field, where the repulsive electromotive forces enable mass transport. The preferred transport pathway is expected to be through the routes of least electrical resistance. A number of factors influence iontophoretic transport including current, voltage, time applied, skin pH, molecular size and structure of the drug, its charge, the concentration of the drug, the presence of competing ions or permeation enhancers in the formulation, the area of the patch, and the integrity of the skin/patch interface. However, the significance of many of these factors may alter if the heat/sound energy is combined with the electromotive force. The preferred sequence of the different energy pulses applied (alternately and/or simultaneously) on a given transdermal drug formulation identifies an experimentally determined/programmable pulsing sequence to optimize/maximize drug permeation. In this way, one may be able to accomplish rapid onset or offset for transdermal drug delivery for a variety of drugs and even the combination of the different drugs in highly controllable and programmable fashion. The proposed active drug transdermal drug delivery technology enables the delivery of molecules that are hard to permeate through skin (insulin and vaccines), rapid delivery (like an injection), pulsatile delivery (like nicotine in smoke/inhalation) and additionally it gives highly precise/predictable control over local vs. systemic drug delivery and pharmacokinetic profiles. Combining above mentioned active transportation mechanisms, with an array of microneedles 8 offers an yet powerful route for precisely controlling the pharmacokinetics of small and large drug molecules, especially proteins, peptides, nucleotides, ribozymes, dsRNAs, RNAi, siRNAs, and vaccines.

Recent advances in printed electronics/microneedle arrays and transdermal drug delivery are expected to simplify the patch design and minimize the patch size. Printed electronics is a relatively new technology that prints conductive and semi-conducting elements using a simple and commonly used printing equipment such as inkjet, screen printing, flexography, gravure, and offset lithography on a common media such as paper, polymers, plastic and textiles. Therefore, printed electronics is expected to facilitate widespread use of very low-cost electronics for applications not typically associated with conventional (i.e., silicon-based) electronics, which include medical diagnostics and disposable transdermal electronic patches such as being proposed in this venture. Further in addition and as discussed earlier, the microneedles arrays with sharp tips could be made in several ways such as adapted microelectromechanical masking, etching, perforation using lasers, photolithography, molding and so on.

FIG. 1 shows a schematic representation of active transdermal drug delivery system as proposed the energy/power is provided by a battery and/or a capacitor (a). The controller unit (b) modulates the input power and turns it into required/programmed energy pulses, which will be received by the converter that is either part of the transdermal patch or exogenous to it (c). The drug from the patch will be delivered to the skin upon activation of the device (d).

Figure 2:
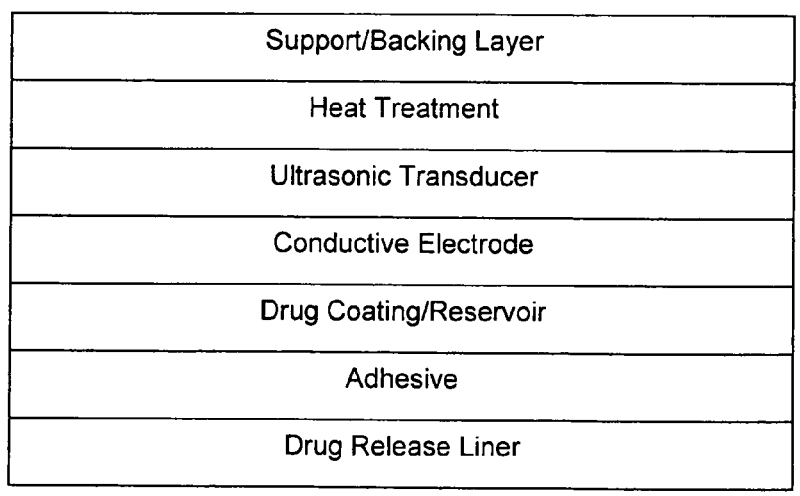
FIG. 2 illustrates the schematic representation of various components present in the transdermal patch in different layers in accordance with the present invention.

On the other hand the FIG. 2 illustrates a representation of various components present in the transdermal patch, as shown in different layers (for clarity.) The sequencing of the various layers could be altered and does not necessarily have to be in the order shown above. Further multiple layers/components (at least two or more) of the patch could be imbedded into a single layer or could form physically distinct layers (exogenous). The drug layer could be a reservoir 5, or part of coating formulation (including polymeric binders, excipients, and adhesive matrix) or a membrane matrix or hybrid form of the above. Finally, some of the above layers may be passive for certain drug delivery applications, for example one could transport certain drugs/formulations using heat and ultrasonic energy without applying iontophoresis.

The support material 3 for transdermal patch is made up of a thin flexible sheet made of polymer, or rubber, or resin, or textile, or a thin metal acceptable for medical applications. At least a part of the support material may have some kind of adhesive 6 to stick it to the skin. Support material could be based on an array of microneedles. The patch can be of any shape as desired by the user and may be perforated. It can be in the shape of a tattoo for giving an aesthetic look to the patch.

The device includes four major components: power source, controller, converter and the patch. A controller (based on micro processor) unit controls the sequence, intensity and timing of the distinct energy inputs.

The power source includes a current source, such as a battery/capacitor of input range of 2V to 1500V and current rating of 0.01 mA-15 mA and a current controller or any external source. The input power source 14 may be in the form of alternate current (AC) or direct current (DC) but preferably a battery and/or a capacitor. Further the input power unit is configured for delivering steady potential of range 0-1500V. The battery/external source is connected to the other components like controller, converter, sensors 15 and the patch receives the correct amount of current for a proper transdermal delivery of drug. The current source connected is of range 0.001 mA-20 mA. The preferable current rating for the active transdermal patch disclosed herein is 10-12 mA. Further the current controller controls the current output only and maintains the threshold current limits of the further connected components. The power source is also fitted with mechanical switches to prevent any current drain during the unused condition and/or efficient use of the patch since one of our objects of the present invention is to provide an electronic patch for multiple use.

The input power source is electrically coupled to the patch using electronic interconnectors, such as a printed flexible circuit, metal foils, wires, tabs or electrically conductive adhesives. When connector is in a connected state, the power source, the delivery components like the resistive coating/pattern for heat, piezoelectric transducers 13 for ultrasonic vibrations, and conductive conduits for converting the current into emf, the control circuitry and the patient's skin form a circuit. In an alternative arrangement, the controller further comprise a transceiver operable and remotely connected to a patch, which is also comprising of a transceiver/receiver for the communication with the said controller configured for an improved and efficient transdermal drug delivery such as hereunder described. A person skilled in the art can appreciate the implication of such transceivers in the transdermal drug delivery system, which makes the system versatile irrespective of any physical constraints. Under such condition the input power source of the patch is made separate and is operably connected to the said transdermal patch.

The controller as described above includes a programmable microprocessor 11, which handles the various transdermal drug delivery conditions. The microprocessor is provided with a programmable software 12 configured for providing the intensity, sequence, nature, and timing information for the different energies supplied to the said patch. As discussed above the different energies include heat, ultrasonic vibrations, electromotive force etc. The intensity, sequence, nature of skin of the patient and drug involved and the time limit for the drug delivery are the major factors/variables involved in the programming of the microprocessor configured for the transdermal drug delivery. Accordingly, as per the object of the present invention the proposed device involve an improved method for the transdermal drug delivery so that the user of the device has greater control of the device, as well as increases the flexibility and reliability. The program of the processor is based on one or more of the above-described factors like skin impedance, skin's pH or the amount of skin perspiration, or both, drug characteristics, delivery timings and/or certain environmental conditions.

The different factors which are managed by the controller using the software program include the temperature, rate of heating, duration of heating, the ultrasonic energy, frequency, intensity, and its duration for the patch inclusive or non inclusive of the microneedles. Further the various electronic factors associated with active transport of the charged drug, such as the power source voltage, current, duration of voltage/current pulses, the type and the surface area of the converters, use of the constant or pulsed DC current, pulse width and the frequency. The various physiological considerations for the treatment of skin tissue, such as its permeability and sensitivity to each particular drug type, as well as the electrical property of the skin tissue. Further complexity arises from the fact that many of these factors vary from patient to patient and even as to the same patient as a function of specific body location receiving the therapy, duration of therapy or therapeutic drug type. Some or all of the transducers and energy converters could be part of controller unit and/or part of the skin patch. As the skin patch is a disposable unit, the electronic circuitry associated with it would be designed to be optimal or inexpensive. For example, both the ultrasonic transducer 1 and heating element 2 could be part of the controller unit (for repeated use) and act upon the skin patch when it is activated. The printed electrodes 4 (for iontophoresis) and resistance circuit (for heating) could be made part of the skin patch as the cost associated with such elements is minimal.

The active transdermal drug delivery system comprise of the patch which is configured for transdermal delivery of an admixture of pharmaceuticals, cosmetics and/or nutraceuticals for the therapeutic and/or non therapeutic purposes. The pharmaceuticals are selected from the group consisting of analgesic agents, anti-arthritic agents; anti-arrhythmic agents anti-asthmatic agents, anesthetics, anticonvulsants, antidepressants (& anti-anxiety drug), antibiotics, anticancer agents antidiabetic agents, anticholinergic antagonists antidotes, antiviral agents; anti-inflammatory agent, antiglaucoma agents antiemetics, antihistamines, antipanic agents anti-infective agents, antineoplastics, antiparkisonian drugs, antirheumatic agents, antipsychotics, appetite stimulants and suppressants; attention deficit disorder (ADD) and attention deficit hyperactivity disorder (ADHD) drugs, cholesterol-lowering agents, anxiolytics, appetite stimulants and suppressants, blood modifiers, cardiovascular agents, central nervous system stimulants, drugs for Alzheimer's disease management, drugs for cystic fibrosis management, diagnostics, dietary supplements, drugs for erectile dysfunction, gastrointestinal agents, hormones, drugs for the treatment of alcoholism, drugs for the treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, opthalmic preparations, osteoporosis preparations, prostaglandins, respiratory agents, sedatives and hypnotics, skin and mucous membrane agents, smoking cessation aids, Tourette's syndrome agents, urinary tract agents, vertigo agents, vaccines, polynucleotides, ribozymes, herbal remedies, nutritional agents.

Examples of anesthetic include ketamine and lidocaine.

Examples of anticonvulsants include compounds from one of the following classes: GABA analogs, tiagabine, vigabatrin; barbiturates such as pentobarbital; benzodiazepines such as clonazepam; hydantoins such as phenyloin; phenyltriazines such as lamotrigine; miscellaneous anticonvulsants such as carbamazepine, topiramate, valproic acid, and zonisamide.

Examples of antidepressants include amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, venlafaxine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine; adrafinil, amesergide, amisulpride, amperozide, benactyzine, bupropion, caroxazone, gepirone, idazoxan, metralindole, milnacipran, minaprine, nefazodone, nomifensine, ritanserin, roxindole, S-adenosylmethionine, escitalopram, tofenacin, trazodone, tryptophan, and zalospirone.

Examples of antidiabetic agents include insulin, pioglitazone, rosiglitazone, and troglitazone.

Examples of antidotes include edrophonium chloride, flumazenil, deferoxamine, nalmefene, naloxone, and naltrexone.

Examples of antiemetics include alizapride, azasetron, benzquinamide, bromopride, buclizine, chlorpromazine, cinnarizine, clebopride, cyclizine, diphenhydramine, diphenidol, dolasetron, droperidol, granisetron, hyoscine, lorazepam, dronabinol, metoclopramide, metopimazine, ondansetron, perphenazine, promethazine, prochlorperazine, scopolamine, triethylperazine, trifluoperazine, triflupromazine, trimethobenzamide, tropisetron, domperidone, and palonosetron.

Examples of antihistamines include astemizole, azatadine, brompheniramine, carbinoxamine, cetrizine, chlorpheniramine, cinnarizine, clemastine, cyproheptadine, dexmedetomidine, diphenhydramine, doxylamine, fexofenadine, hydroxyzine, loratidine, promethazine, pyrilamine and terfenidine.

Examples of anti-infective agent include compounds selected from one of the following classes: antivirals such as efavirenz; AIDS adjunct agents such as dapsone; aminoglycosides such as tobramycin; antifungals such as fluconazole; antimalarial agents such as quinine; antituberculosis agents such as ethambutol; β-lactams such as cefinetazole, cefazolin, cephalexin, cefoperazone, cefoxitin, cephacetrile, cephaloglycin, cephaloridine; cephalosporins, such as cephalosporin C, cephalothin; cephamycins such as cephamycin A, cephamycin B, and cephamycin C, cephapirin, cephradine; leprostatics such as clofazimine; penicillins such as ampicillin, amoxicillin, hetacillin, carfecillin, carindacillin, carbenicillin, amylpenicillin, azidocillin, benzylpenicillin, clometocillin, cloxacillin, cyclacillin, methicillin, nafcillin, 2-pentenylpenicillin, penicillin N, penicillin O, penicillin S, penicillin V, dicloxacillin; diphenicillin; heptylpenicillin; and metampicillin; quinolones such as ciprofloxacin, clinafloxacin, difloxacin, grepafloxacin, norfloxacin, ofloxacine, temafloxacin; tetracyclines such as doxycycline and oxytetracycline; miscellaneous anti-infectives such as linezolide, trimethoprim and sulfamethoxazole.

Examples of anti-neoplastic agents include droloxifene, tamoxifen, and toremifene.

Examples of antiparkisonian drugs include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinerole, selegiline, spheramine, terguride, entacapone, and tolcapone.

Examples of antirheumatic agents include diclofenac, hydroxychloroquine and methotrexate.

Examples of antipsychotics include acetophenazine, alizapride, amisulpride, amoxapine, amperozide, aripiprazole, benperidol, benzquinamide, bromperidol, buramate, butaclamol, butaperazine, carphenazine, carpipramine, chlorpromazine, chlorprothixene, clocapramine, clomacran, clopenthixol, clospirazine, clothiapine, clozapine, cyamemazine, droperidol, flupenthixol, fluphenazine, fluspirilene, haloperidol, loxapine, melperone, mesoridazine, metofenazate, molindrone, olanzapine, penfluridol, pericyazine, perphenazine, pimozide, pipamerone, piperacetazine, pipotiazine, prochlorperazine, promazine, quetiapine, remoxipride, risperidone, sertindole, spiperone, sulpiride, thioridazine, thiothixene, trifluperidol, triflupromazine, trifluoperazine, ziprasidone, zotepine, and zuclopenthixol.

Examples of anxiolytics include alprazolam, bromazepam, oxazepam, buspirone, hydroxyzine, mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem.

An example of an appetite stimulant is dronabinol.

Examples of appetite suppressants include fenfluramine, phentermine and sibutramine.

Examples of blood modifiers include cilostazol and dipyridamol.

Examples of cardiovascular agents include benazepril, captopril, enalapril, quinapril, ramipril, doxazosin, prazosin, clonidine, labetolol, candesartan, irbesartan, losartan, telmisartan, valsartan, disopyramide, flecanide, mexiletine, procainamide, propafenone, quinidine, tocainide, amiodarone, dofetilide, ibutilide, adenosine, gemfibrozil, lovastatin, acebutalol, atenolol, bisoprolol, esmolol, metoprolol, nadolol, pindolol, propranolol, sotalol, diltiazern, nifedipine, verapamil, spironolactone, bumetanide, ethacrynic acid, furosemide, torsemide, amiloride, triamterene, and metolazone.

Examples of central nervous system stimulants include amphetamine, brucine, caffeine, dexfenfluramine, dextroamphetamine, ephedrine, fenfluramine, mazindol, methyphenidate, pemoline, phentermine, sibutramine, and modafinil.

Examples of drugs for Alzheimer's disease management include donepezil, galanthamine and tacrin.

Examples of drugs for cystic fibrosis management include CPX, IBMX, XAC and analogues; 4-phenylbutyric acid; genistein and analogous isoflavones; and milrinone.

Examples of diagnostic agents include adenosine and aminohippuric acid.

Examples of dietary supplements include melatonin and vitamin-E.

Examples of drugs for erectile dysfunction include tadalafil, sildenafil, vardenafil, apomorphine, apomorphine diacetate, phentolamine, and yohimbine.

Examples of gastrointestinal agents include loperamide, atropine, hyoscyamine, famotidine, lansoprazole, omeprazole, and rebeprazole.

Examples of hormones include: human growth hormone (hGH) testosterone, estradiol, and cortisone.

Examples of drugs for the treatment of alcoholism include naloxone, naltrexone, and disulfiram.

Examples of drugs for the treatment of addiction it is buprenorphine.

Examples of immunosupressives includemycophenolic acid, cyclosporin, azathioprine, tacrolimus, and rapamycin.

Examples of mast cell stabilizers include cromolyn, pemirolast, and nedocromil.

Examples of drugs for migraine headache include almotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Examples of motion sickness products include diphenhydramine, promethazine, and scopolamine.

Examples of drugs for multiple sclerosis management include bencyclane, methylprednisolone, mitoxantrone, and prednisolone.

Examples of muscle relaxants include baclofen, chlorzoxazone, cyclobenzaprine, methocarbamol, orphenadrine, quinine, and tizanidine.

Examples of nonsteroidal anti-inflammatory drugs include aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib.

Examples of opioid drugs include alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Examples of other analgesic drugs include apazone, benzpiperylon, benzydramine, caffeine, clonixin, ethoheptazine, flupirtine, nefopam, orphenadrine, propacetamol, and propoxyphene.

Examples of opthalmic preparation drugs include ketotifen and betaxolol.

Examples of osteoporosis preparation drugs alendronate, estradiol, estropitate, risedronate and raloxifene.

Examples of prostaglandin drugs include epoprostanol, dinoprostone, misoprostol, and alprostadil.

Examples of respiratory agents include albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, and pirfenidone Examples of sedative and hypnotic drugs include butalbital, chlordiazepoxide, diazepam, estazolam, flunitrazepam, flurazepam, lorazepam, midazolam, temazepam, triazolam, zaleplon, zolpidem, and zopiclone.

Examples of skin and mucous membrane agents include isotretinoin, bergapten and methoxsalen.

Examples of smoking cessation aids include nicotine and varenicline.

An example of a Tourette's syndrome agent includes pimozide.

Examples of urinary tract agents include tolteridine, darifenicin, propantheline bromide, and oxybutynin.

Examples of vertigo agents include betahistine and meclizine.

Examples of cosmetics include but not limited to collagen, Botulinum toxin (bottox), alpha hydroxyacids, alpha ketoacids, polymeric hydroxyacids, moisturizers, collagen, marine extract, and antioxidants such as ascorbic acid (vitamin C), tocopherol (Vitamin E), and retinol (vitamin A), and/or cosmetically acceptable salts, esters, amides, or other derivatives thereof. Cosmetic agents include those that are capable of improving oxygen supply in skin.

Examples of vaccines include flu/influenza vaccines, vaccines for hepatitis A, B, C, the measles-mumps-rubella (MMR) vaccine, the tenaus-diphtheria vaccine, the varicella (chickenpox) vaccine, the pneumococcal vaccine, and the meningococcal conjugate vaccine, and others.

Examples of polynucleotides include therapeutic DNA

Examples of ribozymes, dsRNAs, siRNA, RNAi, mRNA and related gene therapy vectors Examples of herbal remedies include neem, turmeric, sandal etc.

Examples of nutritional agents include vitamins, minerals.

Further there is provided a plurality of converters for the transformation of the current energy to the different aforesaid energy forms. The converter uses high resistance coatings/patterns or materials for converting electrical energy into heat energy. The patch utilizes the resistive pattern for the transformation of the input energy provided by the controller to heat energy of the range between 25-200° C. and preferably 30-60° C. In general, whenever the high temperatures (>100° C.) are used the heating duration/pulses will be minimized, preferably to below a second or in the order of milliseconds to prevent degradation of the drug/cosmetic formulation and to avoid any possible irritation or injury to the skin. The preferred range for the heat energy (for duration above one second) for the active patch disclosed herein is below 50° C. Also there is provided piezoelectric transducer which produce ultrasound vibrations of frequency range 20-100 kHz. The optimum range for the disclosed active patch is 20-25 kHz. The conductive conduits are used to convert current into EMF. The said components may be reusable or disposable with the said patch. From the recent advances in cheap printed electronics, it is possible to device such small patterns to serve the objectives as set out in the aforesaid paragraphs. The printed electronics is a relatively new technology that prints conductive and semi-conducting elements using a simple and commonly used printing equipment such as inkjet, screen printing, flexography, gravure, and offset lithography on a common media such as paper, plastic and textiles.

The patch is attached to the patient's skin using adhesives or a strap or both. The present disclosed transdermal drug delivery device includes a patch comprising therapeutically active drug formulation in different forms: a) Drug coating layer/matrix type, where the drug dissolved in a solvent or dispersed in a polymer, e.g., cellulose, polyvinylpyrrolidone, polyethylene glycol, along with excipients and deposited onto a substrate in a matrix form. Alternately, drug could be deposited along with an adhesive and/or in a gel matrix. The drug coating could comprise either a single layer or multiple layers involving therapeutic agents, excipients, adhesives and/or drug release controlling layers. The multiple layer might contain non therapeutic layer(s) e.g. chemical enhancers etc. b) Reservoir type, where the drug formulation is stored in a liquid compartment containing a drug solution (dissolved or suspension). The release of drug from the reservoir could be accomplished through several mechanisms upon activation of the converters (Examples also includes removal of protective liner 7 just before activation or puncturing an orifice at the time of activation). The size and number of the reservoirs could be changed significantly depending upon the use. Further in an exemplary embodiment the array of microneedles/(micro-reservoirs) are used to hold the drug formulation into it. c) A membrane matrix type, where a membrane additionally controls the release of drug from drug coating layer (a) and/or drug reservoir (b). Finally, the drug formulation or composition will be varied depending upon the targeted drug physical/chemical properties, pharmacokinetic profiles and therapeutic requirements. The active reservoir should comprise at least one orifice or a drug permeable membrane or a protective film/coating which controls the rate at which the drug is delivered to the skin upon activation. There may be a plurality of mechanisms in the reservoir configured for the delivery of the drug to the skin on being activated by the controller. The active reservoir is configured for the steady supply of the drug to the transdermal tissues. The reservoir may be comprised of a open volume space, a gel on a flat planar surface which can be treated with selected therapeutic drug for subsequent release or reaction or a permeable solid structure such as a porous polymer. The reservoirs may be self dissolvable e.g. in case of coatings. The patch is removable/disposable and electrically connectable to the controller, and delivers the drug to the patient when the patch is in contact with the patient's skin and the device is activated. There can be a plurality of active drug formulation matrices/reservoirs and the drug delivery can be programmed/scheduled accordingly. There is also provided a support material for transdermal patch which is a thin flexible sheet made of polymer, or rubber, or resin, or textile, or a thin metal acceptable for medical applications. Also, at least a part of the support material may have some kind of adhesive to stick it to the skin and may be perforated. Optionally, the support material provides backing and protects the patch from the outer environment. Further the transdermal patch may also be provided with an outer protective coating/sheet or liner or tab, which is removed prior to use.

The patch comprises an extending tab, which connects to the controller. The controller is configured to activate the reservoir simultaneously for the supply of drug at a particular moment of time and/or when the controller is switched from the off to an operational active state. This switching may also be caused by electrically activating an activation signal circuit connected to the controller As per an embodiment, the active drug reservoir could be an array of microneedles.

The drug coating layer/reservoir matrix in the skin patch is so designed that they remain in contact with patient's skin, while receiving distinct energy pulses from the controller/converters. The skin patch holding the drug may be perforated in such a way that heat and ultrasound energy are efficiently transferred to the skin through the drug matrix. Generally, a thin layer of the medicament in the form of a gel and or in other desired form is available in the active reservoirs and is also present in between the skin and the converters (or energy transducers). The presence of the medicament, in the form of gel or in other desired form, between the skin and the converter is automatically provided during the process of application of the said active transdermal patch over the skin. The converters (or energy transducers) are so designed/pulsed that they do not cause any damage to the skin due to excessive heat, vibration, shocks etc. . . . As discussed earlier, the patch may further comprise of a plurality of microneedle arrays configured to pierce through stratum corneum for the controlled delivery of the medicaments. The microneedles arrays are present at the lower most end of the patch where it is in contact with the skin. The upper end of the needles are in contact with the reservoirs and the converters/energy transducers as described above so that the microneedle array can subjected to the heat/ultrasonic vibrations etc. A person skilled in the art will be able to understand and appreciate the efficacy and the synergistic effect in the necessity of such arrays working in conjunction with the different energy converters associated with a pre programmed definitive drug delivery profile. The converters are controlled by the controller which is so pre programmed (as described earlier) that will not in any way cause any damage to the skin. The converters are activated by the connected controller and they are configured to operate in isolation and/or simultaneously. A current source is also connected to the converters. When current passes through the convertors and are activated by the controller, the drug contained in the active reservoir is delivered through the skin and into the patient in a controlled manner. As per one of the embodiment of the present invention the controller is configured for activating the plurality of energy transducers simultaneously with respect to the different active reservoirs so as to perform the controlled transdermal drug delivery. Therefore one of the exemplary objective of the present invention, which is to minimize the skin patch size (surface area) for certain applications by taking advantage of rapid/active drug delivery profiles obtained from the proposed transdermal drug delivery system is fulfiled. Still further embodiment of the present invention discloses the provision of providing the different combinations of drugs, which can be induced transdermally simultaneously.

The controller has a housing, and has an opening to accommodate/electrically connect the inserted patch. The housing also has connection arrays of electric terminals to which the control circuitry and power source are electrically connected, and are preferably mounted with the electric circuits on a printed circuit board. The plural, spaced apart electrical terminals electrically connect to the respective converters/energy transducers that may present inside the patch. While, the plural, spaced apart electrical terminals electrically connect the power source and electrical connectors to the control circuitry. Further, it may be appreciated that the patch insertion and release mechanisms may take any known form, so long as the patch tab is capable of being mechanically and electrically connected to and disconnected from the controller In accordance with one of the embodiment there is provided a timer in the controller which can regulate the drug delivery timings. The timings for the activation of the plurality of converters connected is under condition of the simultaneous use of the converters is possible with the timer. In addition as per another embodiment of the present invention there is provided a feedback control mechanism which provides further control over the medicament delivery. The transdermal drug delivery system as disclosed herein further comprise of sensors like tissue glucose, blood pressure, medicament level indicator or heart rate sensors etc present a feedback mechanism to the controller to further improve the drug delivery mechanism. The controller can be thus be further programmed taking into consideration the feedback data to provide improved and safe delivery of drugs. The controller is also configured for the recordal of the data provided by the sensors and is retrievalable at any instant of time.

Further in addition, in a preferred embodiment, the controller may be pre programmed to allow the patient to trigger the delivery of the pre determined amount of drug present in the plurality of the connected reservoirs from time to time to the patch. The pre programming of the controller is done by activating the different convertors for a particular duration/magnitude/sequence to accommodate the different needs. The different drug profiles can be designed accordingly.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

The invention claimed is:

1. An active transdermal drug delivery system for transdermally delivering a drug to a subject, wherein the system comprises:
   a patch configured to be attached to a skin of a subject, wherein the patch comprises:
   a thermal transducer;
   an ultrasonic transducer; and
   an electromotive force transducer; and a layer configured to retain a drug for delivery to the subject;
   a controller operatively connected to the transducers, wherein the controller comprises a programmable microprocessor configured to simultaneously pulse heat in the range of from about 30° C. to about 60° C., ultrasonic vibrations, and an electromotive force to the skin of the subject to transdermally deliver the drug to the subject, wherein a pulse comprises a duration of one second or more.

2. An active transdermal drug delivery system as claimed in claim 1, wherein the layer comprises a reservoir, a coating, or a combination thereof.

3. An active transdermal drug delivery system as claimed in claim 2, wherein the coating comprises multiple layers.

4. An active transdermal drug delivery system as claimed in claim 2, wherein the reservoir comprises multiple micro-reservoirs.

5. An active transdermal drug delivery system as claimed in claim 2, wherein the coating comprises a gel, a cream, an ointment, a dispersion, a liquid or a combination of any of the foregoing.

6. An active transdermal drug delivery system as claimed in claim 1, wherein the patch comprises a removable protective liner or a coating or a seal.

7. An active transdermal drug delivery system as claimed in claim 1, wherein the patch comprises a support material.

8. An active transdermal drug delivery system as claimed in claim 1, comprising an input power source operatively coupled to the transducers, wherein the input power source is configured to provide altering current (AC) or direct current (DC).

9. An active transdermal drug delivery system as claimed in claim 8, wherein the input power source is a battery, a capacitor, or a combination thereof.

10. An active transdermal drug delivery system as claimed in claim 8, wherein the input power source is configured to deliver steady current in a range of 0.001 mA-20 mA.

11. An active transdermal drug delivery system as claimed in claim 8, wherein the input power source is configured to deliver steady potential in a range of 0-1500V.

12. An active transdermal drug delivery system as claimed in claim 1, wherein the thermal transducer comprises high resistance and conductive patterns, coating, or material for converting the electrical energy into heat.

13. An active transdermal drug delivery system as claimed in claim 1, wherein the ultrasonic transducer comprises a piezoelectric device.

14. An active transdermal drug delivery system as claimed in claim 1, wherein the ultrasonic transducer comprises a piezoelectric device configured to deliver ultrasonic vibrations in a range of 20 KHz-100 KHz.

15. An active transdermal drug delivery system as claimed in claim 1, wherein the electromotive transducer comprises conductive patterns or resistive patterns.

16. An active transdermal drug delivery system as claimed in claim 1, wherein,
   the patch comprises a support material, wherein the support material comprises a thin flexible sheet made of polymer, or rubber, or resin, or textile, or a thin metal acceptable for medical applications;
   at least a part of the support material comprises an adhesive; and
   at least a part of the support material is perforated.

17. An active transdermal drug delivery system as claimed in claim 1, wherein the patch comprises a plurality of sensors configured to determine and to provide patient status information operatively coupled to the controller.

18. An active transdermal drug delivery system as claimed in claim 1, wherein the drug-containing layer comprises a reservoir or a coating formulation comprising polymeric binders, excipients, an adhesive matrix, a membrane matrix or a combination of any of the foregoing.

19. An active transdermal drug delivery system as claimed in claim 18, wherein the patch comprises at least two drug-containing layers.

20. An active transdermal drug delivery system as claimed in claim 1, comprising electronic interconnections operably connecting the controller and the patch.

21. An active transdermal drug delivery system as claimed in claim 1, wherein the controller and the patch comprise wireless connections.

22. An active transdermal drug delivery system as claimed in claim 1, wherein the controller comprises a memory configured to store drug delivery profiles.

23. An active transdermal drug delivery system as claimed in claim 22, wherein the drug delivery profiles are based on disease, doses, time, skin permeability, medicament, environment characteristics and the subject.

24. An active transdermal drug delivery system as claimed in claim 1, wherein the system is configured for local drug delivery or for systemic drug delivery.

25. An active transdermal drug delivery system as claimed in claim 1, wherein the layer further comprises a vitamin, a mineral, a cosmetic, a nutraceutical, or a combination of any of the foregoing.

26. An active transdermal drug delivery system as claimed in claim 1, wherein the drug is selected from the group consisting of analgesic agents, anti-arthritic agents, anti-arrhythmic agents, anti-asthmatic agents, anesthetics, anticonvulsants, antidepressants, anti-anxiety drug, antibiotics, anticancer agents, antidiabetic agents, anticholinergic antagonists antidotes, antiviral agents, anti-inflammatory agent, antiglaucoma agents, antiemetics, antihistamines, antipanic agents, anti-infective agents, antineoplastics, anti-parkisonian drugs, antirheumatic agents, antipsychotics, appetite stimulants and suppressants, attention deficit disorder (ADD) and attention deficit hyperactivity disorder (ADHD) drugs, cholesterol-lowering agents, anxiolytics, blood modifiers, cardiovascular agents, central nervous system stimulants, drug for Alzheimer's disease management, drugs for cystic fibrosis management, diagnostic agents, dietary supplements, drugs for erectile dysfunction, gastrointestinal agents, hormones, drugs for treatment of alcoholism, drugs for treatment of addiction, immunosuppressives, mast cell stabilizers, migraine preparations, motion sickness products, drugs for multiple sclerosis management, muscle relaxants, nonsteroidal anti-inflammatories, opioids, other analgesics and stimulants, ophthalmic preparations, osteoporosis preparations, prostaglandins, respiratory agents, sedatives and hypnotics, skin and mucous membrane agents, smoking cessation aids, Tourette's syndrome agents, urinary tract agents, vertigo agents, vaccines, polynucleotides, ribozymes, herbal remedies, nutritional agents, or combinations thereof.

27. An active transdermal drug delivery system as claimed in claim 1, wherein the layer further comprises a cosmetic selected from collagen, Botulinum toxin (bottox) alpha hydroxyacids, alpha ketoacids, polymeric hydroxyacids, moisturizers, marine extract, and antioxidants including ascorbic acid (vitamin C), tocopherol (Vitamin E), and retinol (vitamin A), and/or cosmetically acceptable salts, esters, amides, or a material capable of improving oxygen supply in the skin.

28. A method for performing transdermal drug delivery using the transdermal drug delivery system as claim 1, comprising the steps of:
attaching the patch to the skin of the subject;
inputting electrical energy from a power source to the transducers;
controlling the electrical energy power input to the transducers using the controller to simultaneously pulse heat, ultrasonic vibration, and electromotive force to the layer and to the skin of the subject.

* * * * *